United States Patent [19]

Sgandurra

[11] Patent Number: 4,505,268

[45] Date of Patent: Mar. 19, 1985

[54] SCOLIOSIS FRAME

[76] Inventor: Vicente Sgandurra, 280 W. Park Dr., Sweetwater, Fla. 33173

[21] Appl. No.: 467,317

[22] Filed: Feb. 17, 1983

[51] Int. Cl.³ .......................... A61F 5/00; A61F 5/04
[52] U.S. Cl. .................................. 128/69; 128/92 EA
[58] Field of Search ................ 128/69, 92 R, 92 E, 128/92 B, 92 EA, 92 EC, 92 G, 303 R

[56] References Cited

U.S. PATENT DOCUMENTS

| | | | |
|---|---|---|---|
| 2,593,624 | 4/1952 | Stevens | 128/69 |
| 3,693,616 | 9/1972 | Roaf et al. | 128/69 |
| 3,865,105 | 2/1975 | Lode | 128/69 |
| 3,915,160 | 10/1975 | Lode et al. | 128/69 |
| 4,112,935 | 9/1978 | Latypou et al. | 128/69 |
| 4,185,623 | 1/1980 | Volkov et al. | 128/69 |

FOREIGN PATENT DOCUMENTS

| | | | |
|---|---|---|---|
| 8248 | 2/1980 | European Pat. Off. | 128/69 |
| 441932 | 12/1974 | U.S.S.R. | 128/69 |
| 556793 | 7/1975 | U.S.S.R. | 128/69 |
| 850062 | 7/1981 | U.S.S.R. | 128/69 |

Primary Examiner—C. Fred Rosenbaum
Assistant Examiner—C. W. Shedd
Attorney, Agent, or Firm—John Cyril Malloy

[57] ABSTRACT

A spinal correction assembly of the type primarily designed to correct deformaties of deformity the spine such as curvatures of the spine also known as Scoliosis and/or Kyphosis. A frame is structured to have mounted thereon, a plurality of reduction arms which in turn support spine embracing hook elements whereby the aforementioned components are each structured for adjustable positioning for the purpose of reorienting the spine by applying preselected force at the opposite end of the affected curved portion of the spine and a force in the opposite direction along the length of the curved portion of the spine. These forces serve to reduce or effectively eliminate the curvature wherein the spine embracing hooks are maintained in fixed alignment to one another until additional surgical procedure such as bone grafting is completed and healed.

14 Claims, 37 Drawing Figures

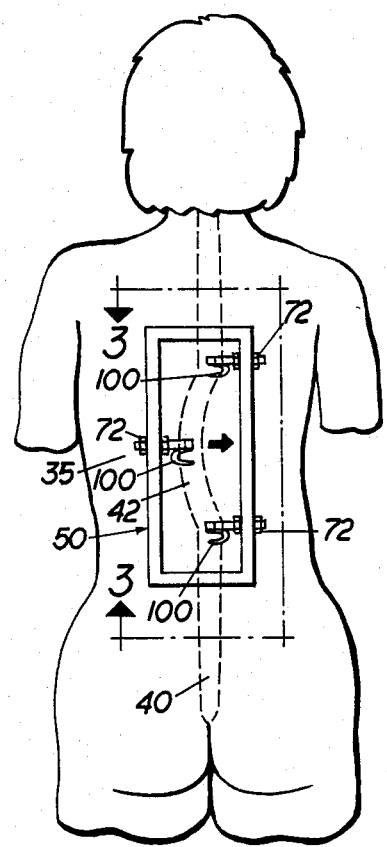
FIG. 1
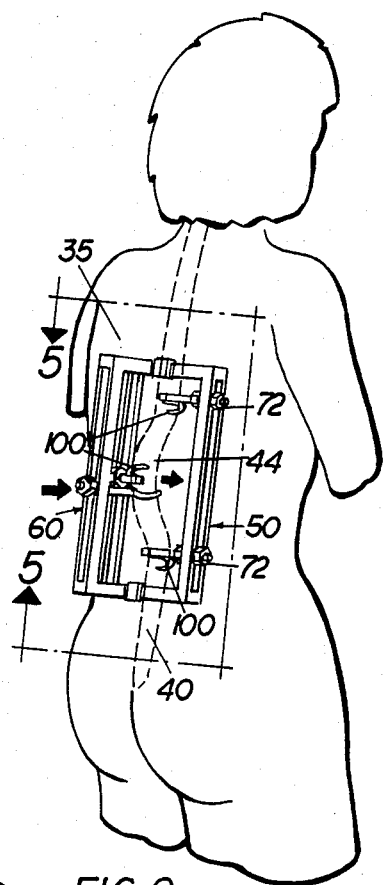
FIG. 2
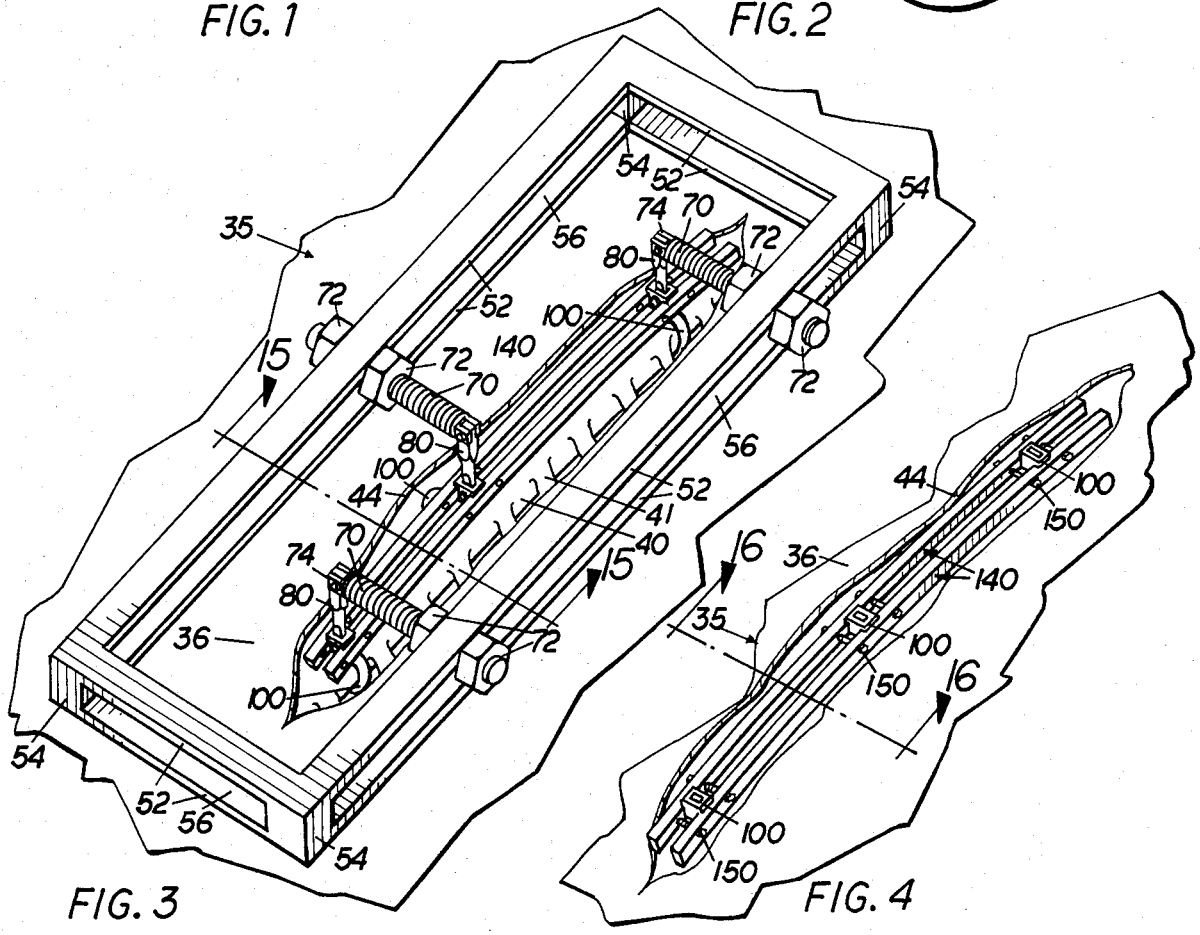
FIG. 3
FIG. 4

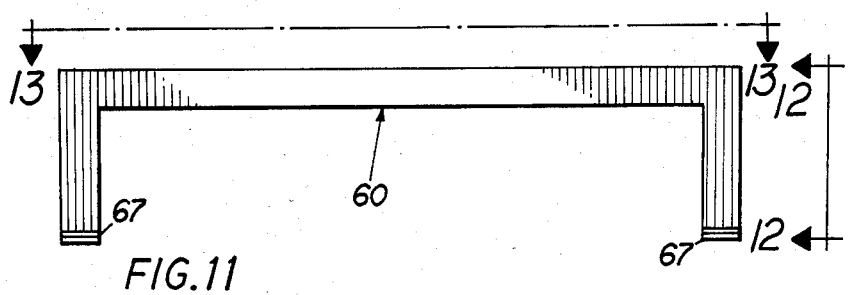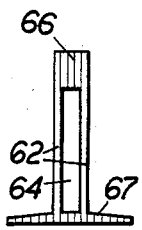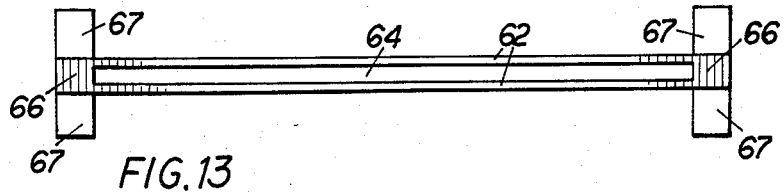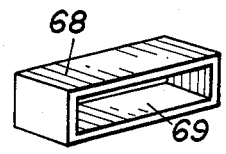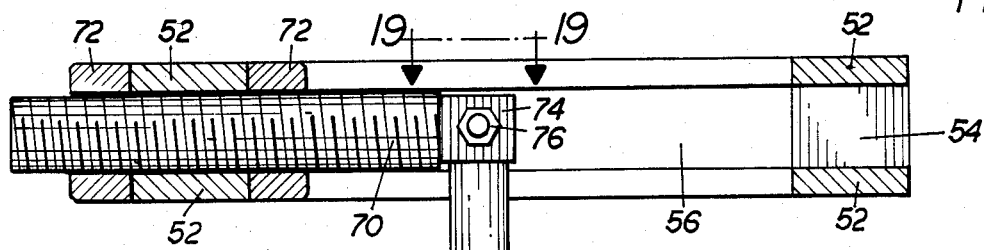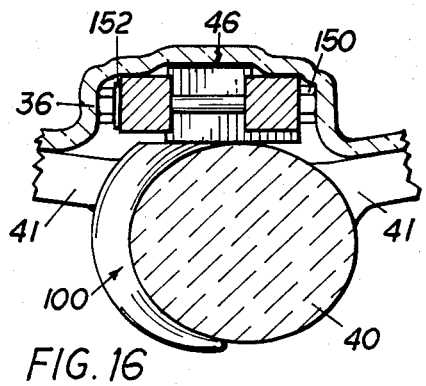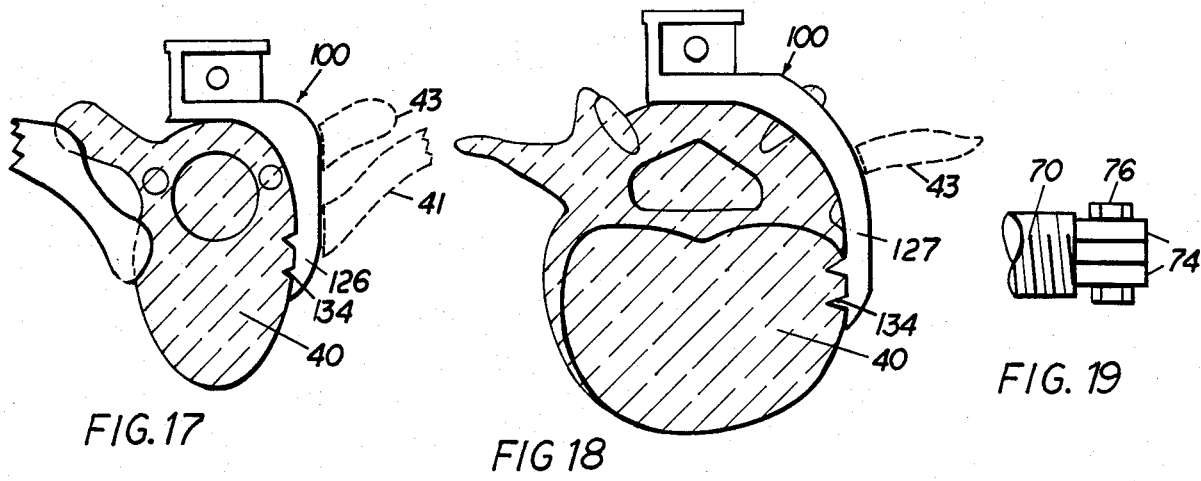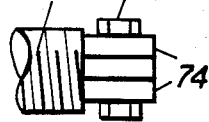

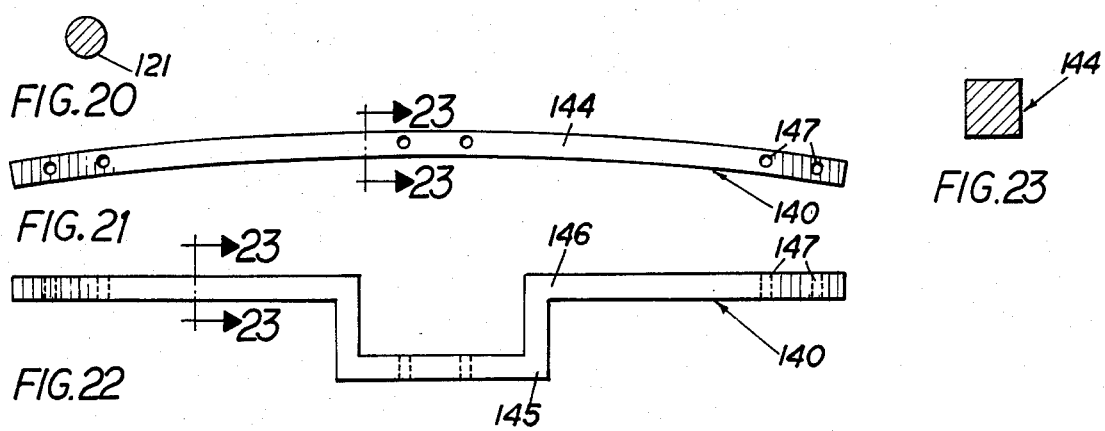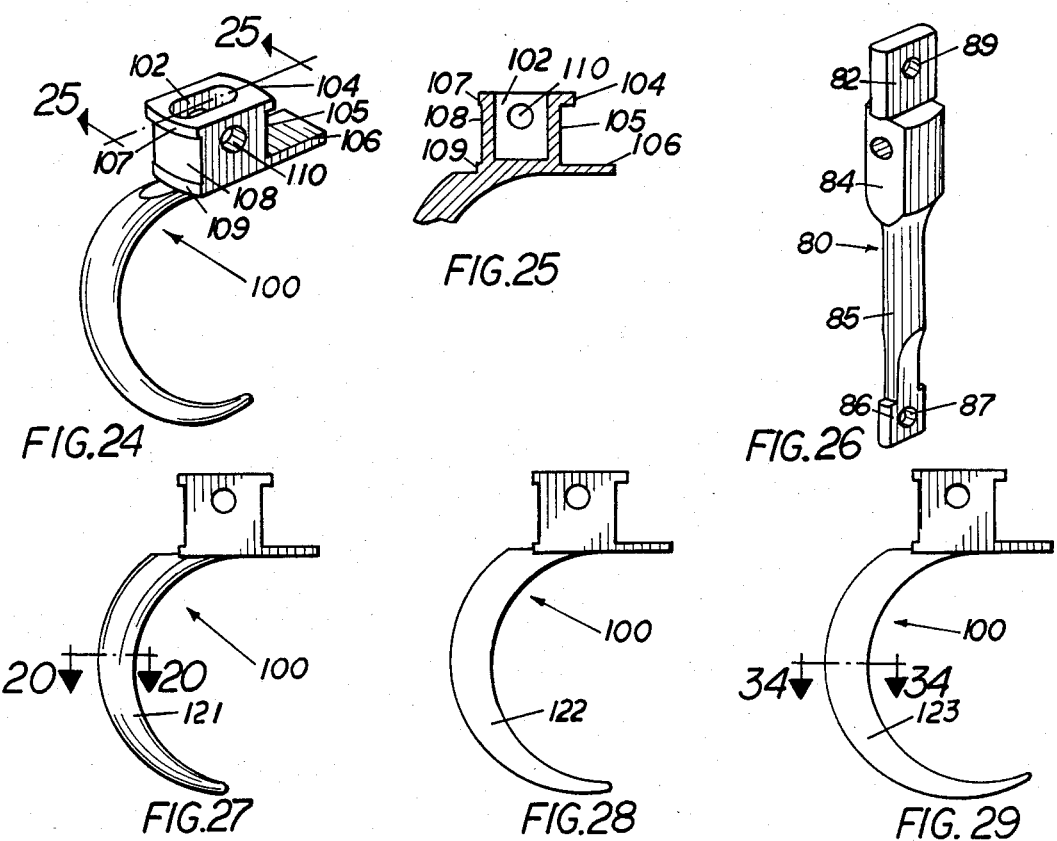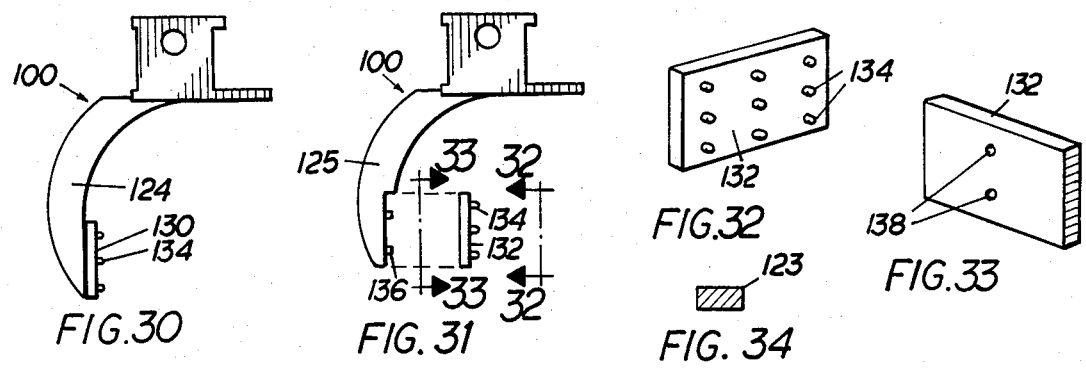

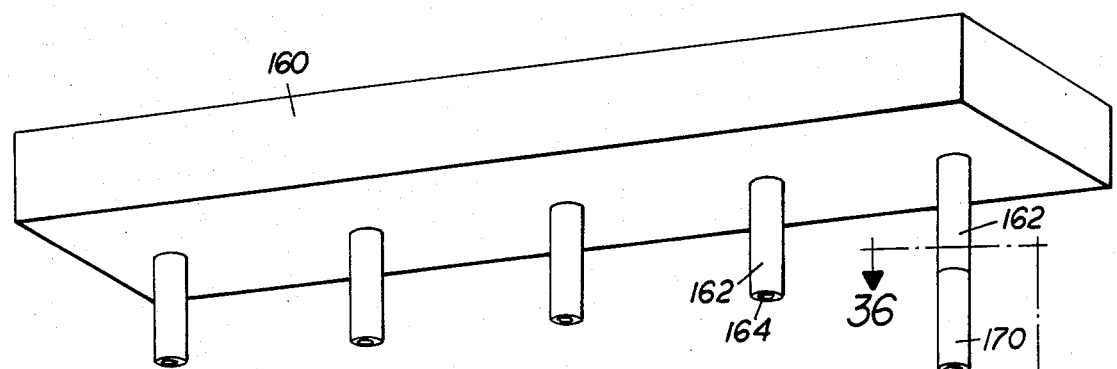
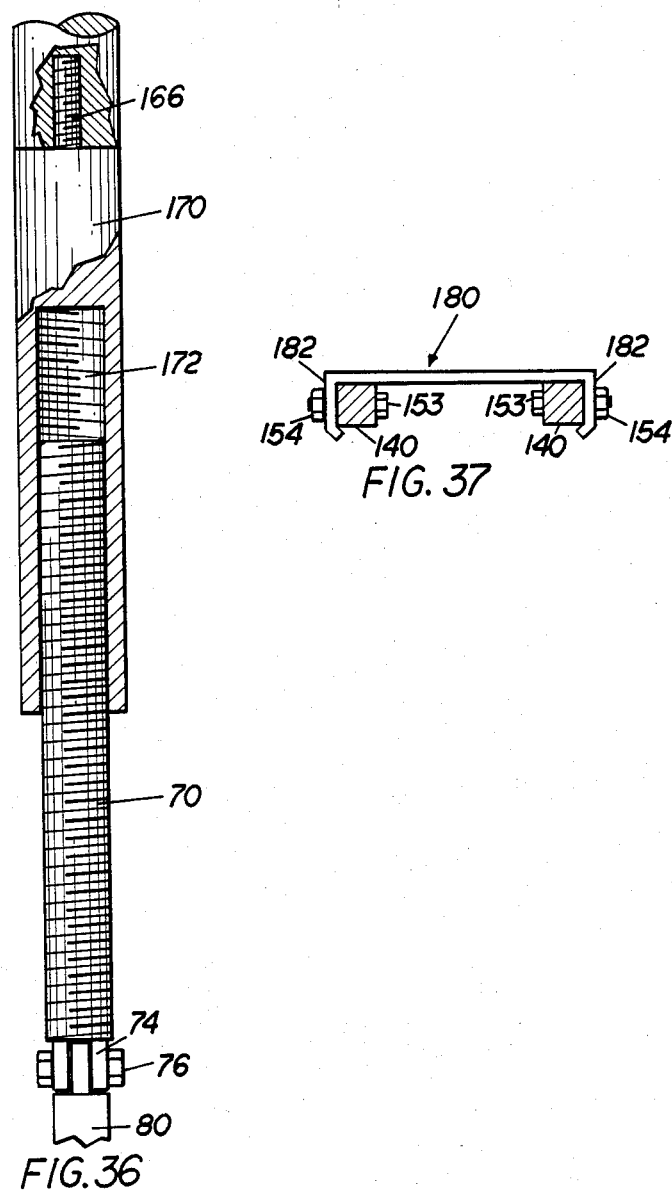

SCOLIOSIS FRAME

BACKGROUND OF THE INVENTION

1. Field of the Invention

This invention is directed towards a supporting frame and force inducing components mounted thereon which are structured to embrace predetermined portions of the spine causing its realignment and the reduction or effective elimination of any undesirable curvature of the spine known medically as Scoliosis and/or Kyphosis.

2. Description of the Prior Art

Spinal deformation known commonly to the layman as curvature of the spine and known medically as Scoliosis is relatively common. Correction of this type of spinal deformity occurs by performing surgical procedures which affect a straightening or alignment of the spine to the extent that the curvature and rotation are reduced as much as possible.

A currently accepted surgical procedure for correcting spinal curvature is known as the Harrington Procedure. This accepted procedure entails the distending of the spine and hopefully, the resulting alignment of the vertebrae into their proper orientation. As practiced, forces are applied to opposite ends of the undesirable curved portion of the spine, causing its distention and hopefully a reduction or elimination of the curvature. Once the spine is disposed in its distended orientation, bone grafting is accomplished between the affected vertebrae. A brace structure is then positioned and maintained in place in support of the affected vertebrae until healing of the grafting procedure is accomplished. While the Harrington Procedure, as currently performed, has effected the desired reduction of curved portions of the spine, at least one problem is inherent to this procedure. When the spine and accordingly the spinal cord surrounded by the vertebrae are oriented into the distended position, the spinal cord must be stretched or distended along with the realignment of the spine. Certain portions of the spinal cord may only accept a certain minimal distention without resulting damage or serious discomfort to the patient. Once the maximum point of distention has been reached by the spinal cord, further distention of the spine and/or affected vertebrae may not proceed. Accordingly, a certain degree of curvature may not be correctable without causing and/or risking severe damage to the spinal cord.

There is a need in the medical profession for an additional, effective surgical procedure and accompanying, complementary instrumentation to solve the problems associated with the correction of Scoliosis and/or Kyphosis. Such a procedure and/or instrumentation should be capable of reducing or eliminating deformity of the spine without undue discomfort to the patient or without the risk of damage to the spinal cord or contiguous soft tissue associated with the affected region of the spine.

SUMMARY OF THE INVENTION

The present invention is directed towards instrumentation primarily designed to correct spinal deformity such as curvature of the spine medically known as Scoliosis and/or Kyphosis. More particularly, the subject invention is directed towards a frame means structured to be positioned in the immediate vicinity of the surgical cite or field and in direct communication with an exposed length of the spine presented after surgical incision. The frame means includes a primary frame having a generally rectangular configuration with open lateral portions defined by spaced apart struts. Between these struts are adjustably mounted deformity reduction means extending into the center opening of the rectangular frame and into communication with the spine at predetermined points along its length. Components of the deformity reduction means include connecting links adjustably and/or removably connected to the distal ends of each arm and connected in depending relation therefrom at substantially right angles to the longitudinal axis of the remainder of the arm. A hook means is removably attached to the distal end of the connecting link.

Each hook means includes a head portion having an interior socket formed therein. The socket is configured to receive the distal end of the connecting link which is similarly dimensioned and configured. The hook portion of the hook means includes a substantially arcuate extension which is dimensioned and configured to embrace and partially surround designated vertebrae of the spine in a manner so as to apply force thereto. Positioning of the various hook means by interconnecting them to deformity reduction means along both lateral portions of the rectangular frame allows opposing forces to be placed at various points along the curved portion of the spine. Adjustment of the deformity reduction means relative to their positions on the frame in a direction colinear to the longitudinal axis thereof creates these forces which are exerted on the spine and eventually the realignment of the deformed curved portion.

After the hook means are aligned, bracing means in the form of two parallel oriented bars are disposed in attached relation to the head portions of each hook means. The bracing bars are conformed into a predetermined longitudinal configuration and are positioned in brace-receiving channels or indentations integrally formed in the head portions of the hook means. The parallel oriented bars are interconnected to one another so as to affix the hook means, and particularly the head portions thereof between the bars. The various hook means are thereby maintained in their aligned relation to one another. At this point, the connecting links are removed from the receiving sockets within the head portion of each hook means and the entire connecting link, deformity reduction means and frame portion are removed from the surgical site. As stated above, the hook means are disposed and maintained in their aligned relation relative to the reoriented spine. Additional surgical procedure is then performed related to the fixing of various affected vertebrae into a predetermined desired position as through the application of bone grafting.

It should readily be seen therefore that the instrumentation of the subject invention is designed to first cause alignment of the affected or curved portion of the spine, maintain the affected vertebrae in the reoriented and aligned position until additional surgical procedure is performed and finally maintain the surgically treated vertebrae portion in their aligned position, through bracing, until healing is accomplished.

When it is intended to use the subject instrumentation, the patient is prepared for surgery in accordance with accepted medical practice. An epidermis lineal incision is made to expose affected predetermined vertebrae of the spine. The primary frame is positioned and the plurality of reduction arm means are attached thereto with hooks being mounted in depending orientation therefrom. Before actual placement of the hook on a given vertebrae is permitted, resection of designated portions of the contiguous rib and transverse process must occur. The space provided by such resection is filled by the arcuate portion of the hook means and more particularly allows embracing of the hook means in at least partially surrounding relation to the designated vertebrae to which force is applied. The hooks are then applied at the designated points along the length of the spine and the deformity reduction means are adjusted relative to their original position on the frame until the deformity has been reduced to the extent necessary or allowed. The bracing means in the form of the parallel oriented bars are then applied to the hook means independent of the reduction arm means and the bars are interconnected to one another so as to maintain the hook means in their aligned, reoriented relation. Additional surgical procedure is performed in the form of bone grafting being applied to the affected vertebrae. The surgical incision is closed with the hooks being maintained in braced orientation and in force application to the predetermined points along the affected length of the spine. Dependent upon the procedure utilized, and whether or not the procedure comprises a one or multi-step process, a cast and/or corset and/or padding is applied to the patient as required. Removal of the bracing bars and force-bearing hook means is accomplished after healing is indicated.

BRIEF DESCRIPTION OF THE DRAWINGS

For a fuller understanding of the nature of the subject invention, reference should be had to the following detailed description taken in connection with the accompanying drawings, in which:

FIG. 1 is a rear plan view in schematic form of the subject invention as applied to the spine of a patient.

FIG. 2 is an isometric view in schematic form of the embodiment of FIG. 1 with an additional embodiment or secondary frame structure added thereto.

FIG. 3 is an isometric view along line 3—3 of FIG. 1.

FIG. 4 is an isometric view of details of the bracing structure of the present invention.

FIG. 11 is a side plan view of the structural features of the embodiment of FIG. 5.

FIG. 12 is an end view taken along line 12—12 of FIG. 11.

FIG. 13 is a top view taken along line 13—13 of FIG. 11.

FIG. 14 is an isometric view of the structural details associated with the secondary frame of FIG. 5.

FIG. 15 is a sectional view in partial cutaway along line 15—15 of FIG. 3.

FIG. 16 is a sectional view in partial cutaway taken along line 16—16 of FIG. 4.

FIG. 17 is a sectional view showing details of the hook means in grasping or embracing relation to a selected vertebrae.

FIG. 18 is a sectional view of another embodiment of the hook means in grasping or embracing relation to a selected vertebrae.

FIG. 19 is an end view in partial cutaway along line 19—19 of FIG. 15.

FIG. 20 is a sectional view taken along line 20—20 of FIG. 27.

FIG. 21 is a front plan view of another embodiment of the bracing means of the present invention.

FIG. 22 is yet another embodiment of the bracing means of the present invention.

FIG. 23 is a sectional view taken along line 23—23 of FIG. 21 or 22.

FIG. 24 is an isometric view showing structural details of the hook means of the present invention.

FIG. 25 is a sectional view in partial cutaway along line 25—25 of FIG. 24.

FIG. 26 is an isometric view of a connecting link of a deformity reduction means of the present invention.

FIGS. 27, 28 and 29 are all front plan views showing structural configurations of the various hook means of the present invention.

FIG. 30 is a front plan view of an additional hook means structure of the present invention.

FIG. 31 is a front plan view in partially exploded form of the structure of FIG. 30.

FIG. 32 is an isometric view along line 32—32 of FIG. 31.

FIG. 33 is an isometric view along line 33—33 of FIG. 31.

FIg. 34 is a sectional view taken along line 34—34 of FIG. 29.

FIG. 35 is an isometric view shown in schematic form of yet another embodiment of the present invention.

FIG. 36 is a sectional view in partial cutaway along line 36—36 of FIG. 35.

FIG. 37 is an end view in partial section of another embodiment directed to means of connecting the bracing bars to one another.

Similar reference characters refer to similar parts throughout the several views of the drawings.

DETAILED DESCRIPTION OF THE PREFERRED EMBODIMENT

Figure 6:
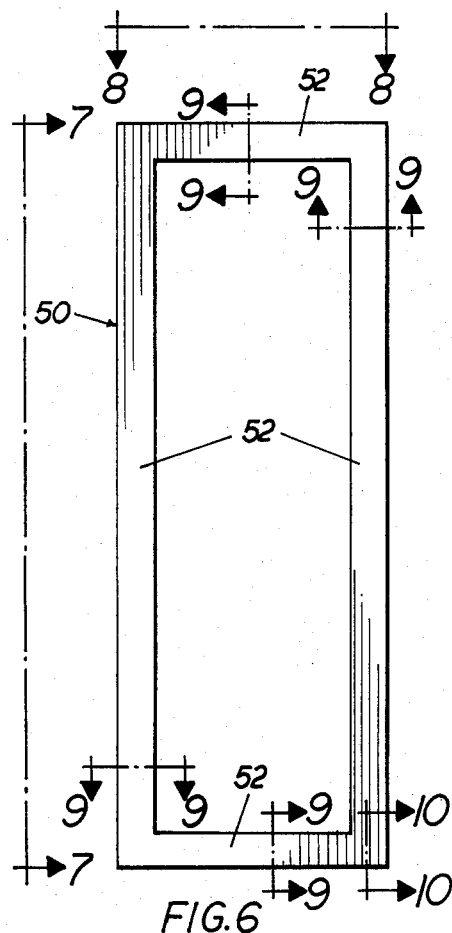
FIG. 6 is a front plan view of the primary frame structure of the present invention.
Figure 7:
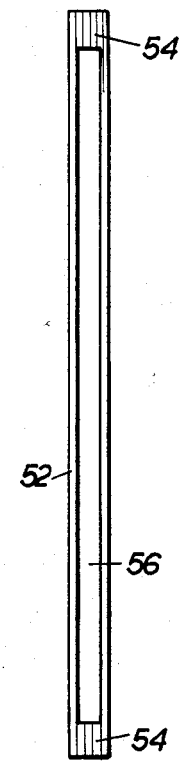
FIG. 7 is a side view of the embodiment of FIG. 6 taken along line 7—7 thereof.
Figure 8:
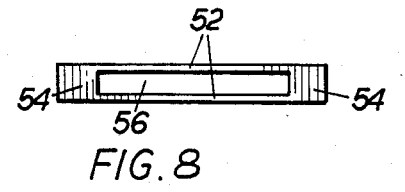
FIG. 8 is an end view taken along line 8—8 of FIG. 6.
Figure 9:
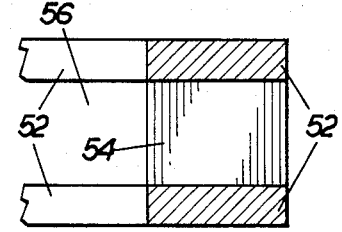
FIG. 9 is a sectional view taken along line 9—9 of FIG. 6.
Figure 10:
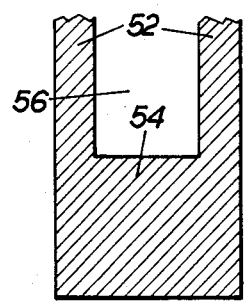
FIG. 10 is a sectional view in partial cutaway along line 10—10 of FIG. 6.

With reference to FIGS. 1 and 2, a patient 35 is represented schematically in a prone or face-down position wherein a frame means generally indicated at 50 is disposed above the skin 36 and over a surgical site. A plurality of deformity reduction means 70 are mounted on the frame 50 and extend inward toward the center of the frame from the lateral sides thereof. These deformity reduction means 70 are connected by a plurality of connectors 72 disposed on opposite sides of the lateral struts 52. Struts 52 define the lateral and end portions of frame 50 and are separated by space 56. (FIGS. 6 and 7). As best shown in FIG. 15, the deformity reduction means 70 includes an elongated externally threaded shaft which is dimensioned to fit between the space 56 separating the two lateral struts 52. The internally threaded connectors 72 are disposed on opposite sides of the struts 52 and serve to maintain the deformity reduction means on the frame in supported position relative thereto. It is of course noted that manipulation of both of the nuts 72 serve to regulate or position the disposition of the deformity reduction means 70 relative to the frame 50 and its position relative to the incision 44 and exposed spine 40.

Again referring to FIGS. 1 and 2, hook means generally indicated as 100 are specifically configured to at least partially embrace selected vertebrae of the spine 40 at various points along the length thereof and apply a "pushing" force thereto in a predetermined direction. More particularly, each of the endmost hook means 100 as shown in FIG. 1 embrace predetermined vertebrae of the spine in at least partially surrounding relation thereto. Force is applied or maintained at the points of engagement and accordingly at the points where a given curvature 42 of the spine 40 begins. At least one additional hook means 100 embraces the curvature 42 at a point between the endmost positioned hook means 100. Upon manual adjustment of the connectors 72 relative to the struts 52, a pressure or force is applied to the deformity reduction means 70 and accordingly the connected hook means 100 to the vertebrae of the spine 40. This force is indicated by the directional arrows as shown in FIG. 1 and the curvature of the spine is corrected.

Figure 5:
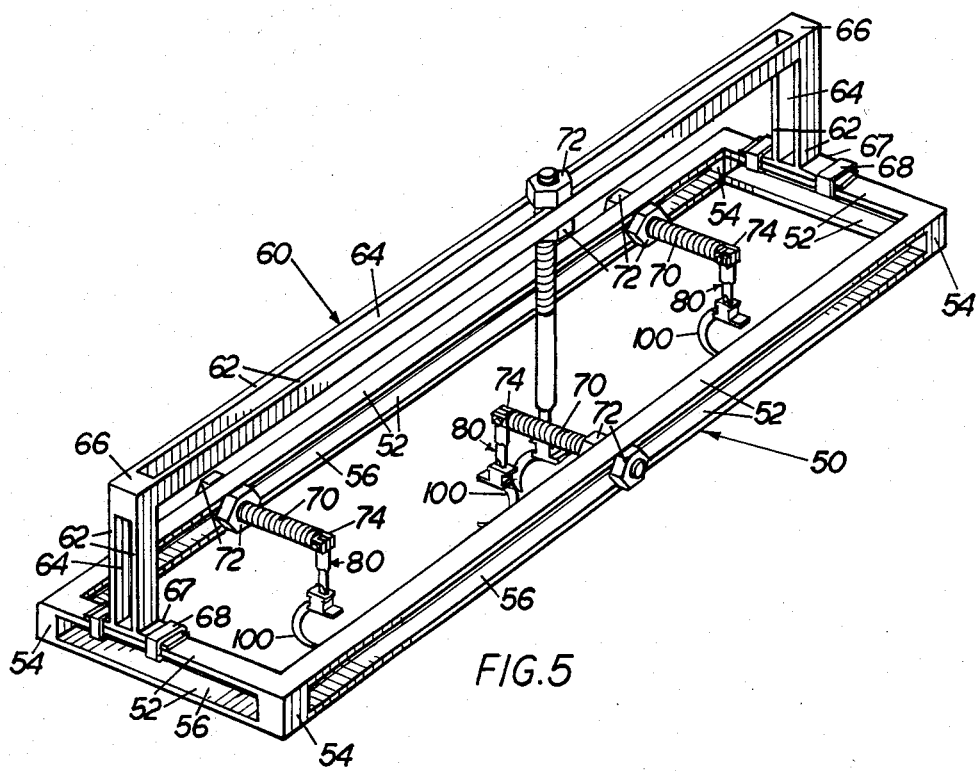
FIG. 5 is an isometric view taken along line 5—5 of FIG. 2 of the present invention.

A second embodiment of the present invention comprises the addition of a secondary frame generally indicated as 60 in addition to the primary frame generally indicated as 50. With reference to FIG. 5, the secondary frame 60 is disposed in perpendicular relation to the primary frame 50 and mounted thereon. Mounting occurs through the provision of tapered flanges 67 (FIG. 12) resting on the upper surface of the end struts 52. Collar means 68 slide along the length of the appropriately positioned end struts 52 and over the tapered flanges 67 so as to maintain the secondary frame 60 in the desired location. Spaced apart struts 62 are secured at opposite ends by integral corner portions 66 wherein space 64 separates these struts 62. Similarly, a deformity reduction means 70 may extend in a depending relation between struts 62 and within space 64. Adjustable positioning of the deformity reduction means 70 is accomplished by manipulation of the connector nuts 72 as stated above.

With reference to FIGS. 2 and 5, the force applied to the engaged points or vertebrae of the spine by the positioning of the deformity reduction means 70 connected to the primary frame 50 occurs in a substantially lateral direction and are applied to correct curvature deformities known as Scoliosis. However, a posterior deformity known as Kyphosis is also common and frequently requires correction. Therefore, there is the necessity for the provision of the secondary frame 60 so as to provide forces and/or pressure on the spine in a posterior direction or in a direction substantially perpendicular to those forces being exerted on the spine by the deformity reduction means 70 and associated hook means interconnected directly to the primary frame 50.

In brief summary, each of the deformity reduction as pictured in FIGS. 1, 2, 3 and 5 are adjustably positioned relative to their original mounting on either primary frame 50 or secondary frame 60. This adjustable positioning is utilized to accomplish force or pressure being brought to bear on predetermined engaged vertebrae of the spine 40. The spine is of course engaged by the hook means 100 interconnected to the distal end of the reduction arm means 70.

This interconnection occurs through the existence of a connecting link structure 80 (FIG. 26). Connecting link 80 includes an elongated shaft 85 having an upper end 82, a lower end 86 and an enlarged portion 84. End 82 is designed to fit between fingers 74 defining the distal end of deformity reduction means 70 (FIG. 19). A central aperture 89 is provided to have a connector element pass therethrough and be secured as at 76 (FIG. 15). As can be seen, connecting link 80 is removably attached to the distal end of the deformity reduction means 70. The opposite end 86 of the connecting link 80 is specifically dimensioned and configured to fit within a socket 102 of the head portion 104 of the hook means 100. A central aperture 87 is formed in the end 86 of connecting link 80 and is alignable with aperture 110 of the head portion of hook means 100. A connector may be placed therein for removable attachment of the end 86 within the socket 102. Positioning of deformity reduction means 70 causes the accordant positioning of connecting link 80 and the predetermined disposition of the hook means 100 relative to the spine 40 or individual vertebrae which it is intended to embrace. The hook means 100 further includes a hook portion including an arcuate extension 121 through 124 (FIGS. 27 through 30) wherein the arcuate extension or hook portion is specifically configured to embrace various vertebrae or various points along the length of the spine. The shape and/or amount of curvature incorporated in the extension of the hook means is dependent upon what vertebrae or location of the spine is embraced. Accordingly, the various structural configurations of the hook portions of the hook means of FIGS. 27, 28, 29 and 30 are represented as the various structures used to embrace the various predetermined points along the length of the spine.

Additional structural features (FIGS. 30–33) include a grasping means in the form of plate 130 being attached to the distal end of arcuate portion 124. The grasping plate has outwardly protruding barbs 134 extending from the surface 132 and into direct grasping engagement with the individual vertebrae to which the hook means 100 is attached. This plate 130 is secured to the indicated end of arcuate portion 124 and 125 by connecting mounts 136 being placed within apertures 138 (FIG. 33) of the plate 132. Such securement may be accomplished by welding or other attachment as indicated.

As best shown in FIGS. 17 and 18, in order to accomplish proper placement of the arcuate portions 126 and 127 of the hook means on a particular vertebrae 40, it is important that the degree of curvature of the arcuate portion 126 or 127 must conform to the overall size of the vertebrae which in turn is dependent upon the particular region or length of the spine being treated. In addition, it is necessary to resection rib portion 41 and transverse process 43. The arcuate portion 126 and/or 127 thereby partially surrounds and embraces the selected vertebrae in the space left by removal of the resectioned rib portion 41 and transverse process 43.

For purposes of clarity, FIG. 17 represents a hook means 100 embracing or engaging a vertebrae generally located in the dorsal area of the spine. FIG. 18 is demonstrative of a hook means 100 embracing a vertebrae in the lumbar region of the spine.

With reference to FIGS. 3, 4, 16, 21, and 22, the bracing means comprises two bars oriented and attached together in substantially parallel relation which in the preferred embodiment are represented as bars 140 having a substantially curved longitudinal configuration (FIG. 21). The bars have spaced apart pairs of apertures 147 through which various connectors 150 are inserted and secured. The bars 140 are utilized to interconnect the various head portions of the hook means 100 once the hook means are properly adjusted relative to the intended force to be placed on the spine. The connectors 150 are disposed on each side of the sandwiched hook means 100 and accordingly the head portion of the respective hook means are secured therebetween in their aligned position. Once the bracing bars 140 are so positioned, the deformity reduction, connecting links and primary and/or secondary frame means may be removed. Due to the presence of the bracing bars 140 the hooks will be maintained in their aligned relation. The forces originally brought to bear on the spine and the various vertebrae thereof will be maintained as long as the bracing bars are in place.

With reference to the curvilinear configuration of the body 144 of the bracing bar 140, this elongated curve is pre-molded or otherwise formed by bending apparatus to adapt to normal posterior convexity of the dorsal region of the spine or when in inverted orientation to the normal lordosis of the lumbar region of the spine.

With regard to the embodiment of FIG. 22, this structure of the bracing bar 140' is utilized in the above noted fashion and in a multi-step process when for instance total correction of the curvature cannot be obtained in a single procedural step. It is not uncommon to require two or more correction steps to accomplish total correction of the deformed curvature of the spine. When a two or more step process is utilized, the bracing bars engage the head portions of a plurality of hook means therebetween in the manner described above. However, the entire pair of bracing bars 140' remain on the outside or exterior of the patient after the incision has been closed. In such an embodiment, the head portions of the hook means extend completely out of the incision into fixed engagement and in aligned relation to one another with the bracing bars 140'. In accordance with this embodiment, adjustment of the hook means remaining in the patient and in engaging relation with the spine may occur after closure of the incision or surgical site. This adjustment may occur in a single additional step or a multi-step process until ultimate correction or alignment of the deformed spine is accomplished.

Additional structural features associated with the hook means 100 (FIGS. 24 and 25) includes channel means integrally formed in the head portion of the hook means. More specifically, outwardly extending top flanges 107 and 104 extend from the main of the head portion in opposite directions. Similarly, a slight lower flange 109 is also provided to extend in spaced apart but parallel relation to flange 107. A much enlarged flange 106 is disposed substantially opposite to flange 109 and extends outwardly from the head portion in an opposite direction. A channel 105 and, to a lesser extent, a channel groove 108 is thereby formed for the positioning and/or partial support of the bracing bars 140 relative to the head portion. However, it should be emphasized that the elongation of flange 106 is provided to provide proper force bearing surface when the hook portion embraces the selected vertebrae and applies a "pushing" force thereon. With reference to FIG. 16, the spine 40 is shown embraced by the arcuate portion of the hook means 100. The head portion thereof is disposed in sandwiched relation between bracing bars 140. Connectors 150 and 152 serve to secure the bars 140 in a parallel relation to one another. Also, the bars 140 are effectively affixed to the head portion of the hook means. Once so positioned, additional surgical procedure can be performed such as bone grafting to maintain the vertebrae in the aligned relation. The entire hook means, bracing bars, and appropriate connectors are maintained within the patient in proper engaged and embracing relation to the spine 40 and a closed incision 46. Healing of the various bone grafts or other surgical procedure performed is allowed. Once alignment is insured by the healing of the surgery, the bracing bars and hook means may be removed from the spine 40.

With regard to FIG. 37, a clamping means generally indicated as 180 is provided to interconnect bracing bar element 140 (or 140'). This clamping means is utilized primarily when the subject procedure is applied to babies, children, or small patients. In such cases, the thickness and consequently the structural integrity of the individual bracing bars 140 is lessened. Using conventional connectors 150 and 152 (FIG. 16) would cause a bending and/or possible distortion of the bracing bars once they are fixed to the head portions of the hook means 100. Accordingly, the clamping means 180 includes its opposite ends 182 disposed in substantially surrounding relation to the outer lateral surface portions of the bracing bars 140 so as to maintain them in attached relation to one another at a fixed, predetermined distance apart. Connector elements 153 and 154 are utilized to interconnect the end portions 182 to the bars 140 as shown in FIG. 37.

With reference to FIGS. 35 and 36, a schematic representation is presented wherein placement of the hook means 100 occurs automatically or more specifically without the physical or manual manipulation of the deformity reduction means 70 relative to either the primary frame 50 or secondary frame 60. In the embodiment shown in FIG. 35, an electrically powered console 160 is provided having a plurality of take-off arms 162 movably secured thereto. 160 is the type of electrical console which, through proper gearing an electronic circuitry is disposed in the ceiling or other applicable location within an operating room. The take-off arms 162 are provided in spaced apart relation to one another wherein such arms are capable of movement in a direction which is both colinear and transverse to the longitudinal axis of the console 160. An adapter portion 170 serves to interconnect the arm reduction means 70 to the power take-off 162 as best shown in detail in FIG. 36. In such embodiment, the deformity reduction means 70 may be externally threaded to movably engage the interior threaded portion 172 of the adapter member 170. Similarly, a threaded shaft 166 can serve to fixedly secure the adapter member 170 to the take-off member 162. Due to the threaded interconnection between the deformity reduction means 70 and adapter member 170, the specific height or position of the deformity reduction means 70 can be regulated by the relative placement of the two members. Rather than a threaded connection as shown in FIG. 36, it could be any type of lever arm and/or ratchet or jack-type assembly which is mechanically well-known but which would accomplish relative movement between deformity reduction means 70 and adapter member 170. In utilization of the embodiment shown in FIGS. 35 and 36, the primary frame and secondary frame 50 and 60 respectively are not utilized. Rather, the hook means 100 is lowered into embracing relation with a selected vertebrae of the spine under treatment. Next the electrical power, through proper take-off or control means, is activated so as to position the entire attached assembly including take-off 162, adapter 170, deformity reduction means 70, connecting link 80, and hook means 100 in either a lateral or longitudinal direction so as to apply proper pushing force to the selected vertebrae in order to correct the curvature and bring the affected vertebrae into proper alignment as set forth above.

What is claimed is:

1. A spinal correction assembly of the type primarily designed to correct deformaties of the spine such as Scoliosis and Kyphosis, said assembly comprising:
   frame means dimensioned and configured for placement on the exterior of the body and in communicating relation with a surgical incision and the exposed spine,
   a pluraity of deformity reduction means each movably mounted on said frame and selectively positionable in communicating relation with the surgical incision,
   hook means removably connected to said deformity reduction means and movably positionable therewith and including a substantially arcuate shaped hooked portion configured for at least partially surrounding relation to selected vertebrae, whereby a plurality of hook means are selectively positioned into force-bearing engagement at spaced apart points along the spine causing its intended reorientation.

2. An assembly as in claim 1 further comprising brace means including two bar elements connected to one another in spaced apart relation and having a plurality of said hook means fixed between said two bar elements in sandwiched relation thereto, said hook means disposed in embracing, force-bearing relation to selected points of the spine, whereby said plurality of hook means are maintained in aligned relation to one another upon removal of selective ones of said reduction arm means.

3. An assembly as in claim 2 wherein said bar elements are connectable to one another at a plurality of predetermined locations along the length thereof, said bar elements positioned in substantially parallel relation to one another with said plurality of hook means fixedly disposed therebetween.

4. An assembly as in claim 3 wherein said two bar elements are substantially equally dimensioned and configured and each of said two bar elements comprises a substantially curvilinear configuration along the length thereof, said curvilinear configuration substantially conforming to a normal posterior convexity of the dorsal region of the spine.

5. An assembly as in claim 2 further comprising clamp means mountable on said two bar elements in embracing substantially overlapping relation thereto, opposite ends of said clamp means each connected to separate ones of said bar elements, whereby said hook means are fixed between said bar elements, the latter secured together by said clamp means.

6. An assembly as in claim 2 wherein said hook means includes a head portion secured to said hook portion, said head portion including spaced apart flange elements extending outwardly from opposite ends thereof in the same direction, said spaced apart flange elements at least partially defining a brace receiving channel, said head portion secured to said brace means between said two bar elements and at least one of said bar elements received within said brace receiving channel, whereby a plurality of said hook means are fixedly secured in aligned relation to one another along the length of said brace means and in force-bearing relation to the spine.

7. An assembly as in claim 6 wherein said connecting link is connected to said base portion and has its distal end structured for removable connection to said hook means.

8. An assembly as in claim 6 wherein said flange elements comprise a first flange and a second flange, said first flange disposed closest to said head portion and between said second flange and said head portion, said first flange extending outwardly from said base portion a greater distance than said second flange, said first flange supportingly engaging said brace means on a surface thereof facing said second flange and positioned to engage the spine along an undersurface thereof facing said hook portion.

9. An assembly as in claim 1 wherein said hook means includes a head portion secured to said hook portion, said head portion comprising socket means formed on the interior thereof and structured to removably receive a substantially correspondingly dimensioned distal end portion of said reduction deformity means therein, whereby said hook means is selectively positionable in force-bearing relation to the spine upon selective positioning of said deformity reduction means on said frame means.

10. An assembly as in claim 1 wherein said hook portion includes grasping means disposed along an inner arcuate surface portion thereof, said grasping means including outwardly protruding barb elements structured to engage selected vertebrae along the length of the spine.

11. An assembly as in claim 1 wherein said frame means comprises a primary frame having a substantially rectangular configuration and including spaced apart struts defining lateral peripheral portions thereof, said deformity reduction means movably connected between said struts and structured for selected disposition of attached hook means, whereby lateral forces applied to selected points of said spine causing reduction of lateral curvature thereof.

12. An assembly as in claim 11 wherein said frame means comprises a secondary frame connected to said primary frame and spaced outwardly therefrom in substantially perpendicular relation thereto, said second frame structured for movably supporting said deformity reduction means and connected hook means thereon, said hook means engaging the spine and applying orienting force thereto in a direction substantially perpendicular to force exerted on the spine by hook means supported by said primary frame means.

13. An assembly as in claim 11 wherein each of said plurality of deformity reduction means comprises a base portion supportingly secured to said frame means and including a substantially elongated externally threaded shaft; two connector elements being internally threaded and movably secured along said shaft into abutting relation to opposite sides of said side struts of said frame means.

14. An assembly as in claim 13 further including a connecting link secured to the distal end of said shaft and depending in angled relation to the longitudinal axis of said shaft, said connecting link disposed and configured for interconnecting said shaft and said hook means.

* * * * *